United States Patent [19]

Lefren et al.

[11] 4,431,427

[45] Feb. 14, 1984

[54] TAMPONS AND THEIR MANUFACTURE

[75] Inventors: Karl E. Lefren, Yorklyn; Seymour Yolles, Newark, both of Del.

[73] Assignee: University of Delaware, Newark, Del.

[21] Appl. No.: 308,291

[22] Filed: Oct. 5, 1981

[51] Int. Cl.³ ............................................. A61F 13/20
[52] U.S. Cl. .................................... 604/285; 604/358
[58] Field of Search ........................ 604/55, 285–288, 604/330, 358, 360, 379, 904

[56] References Cited

U.S. PATENT DOCUMENTS

| | | | |
|---|---|---|---|
| 3,091,241 | 5/1963 | Kellett | 604/285 |
| 3,490,454 | 1/1970 | Goldfarb et al. | 604/285 |
| 3,639,566 | 2/1972 | Naito et al. | 424/37 |
| 3,902,493 | 9/1975 | Baier et al. | 604/285 |
| 3,964,486 | 6/1976 | Blaney | 604/285 |

*Primary Examiner*—C. Fred Rosenbaum
*Assistant Examiner*—Sherri E. Vinyard

[57] ABSTRACT

A tampon having incorporated therein one or more substances, such as one or more physiologically safe organic acids that will maintain a pH of about 4.5 to 2.5 in the absorbed fluids during the use of the tampon, to create a hostile but safe environment to inhibit the growth of pathogenic bacteria, such as *Staphylococcus aureus*, within and on the tampon during its use.

5 Claims, No Drawings

TAMPONS AND THEIR MANUFACTURE

BACKGROUND OF THE INVENTION

Body fluid adsorption devices and more particularly a compressed mass of treated adsorbent substance formed into a tampon, or the like, for insertion into a body cavity and adapted for adsorption and retention of body fluid have been in use for many years. In the case of vaginal tampons, where the menstrual flow varies from 6 to 14 grams during the period of use of a particular tampon, efforts have been made to increase the absorptive capacity while retaining the same size of the product. Efforts have also been made to provide a product with a greater capacity for retaining catamenial fluid against expulsion by squeezing. These efforts have resulted in the treatment of the adsorbent substance when it is cotton fibers as described in U.S. Pat. No. 2,849,000 dated Aug. 26, 1959, as well as to the development of new types of absorbent substances such as the solid, water-swellable, water-insoluble polymeric absorbents described in U.S. Pat. No. 3,669,103 dated June 13, 1972.

The many improvements in the fields of absorption and retention have not only increased the protection (i.e., no leakage or discoloration of clothing, etc.) during the period of use, but has also increased that period of use. This increased period of indwelling has extended the time during which bacterial growth can take place within the tampon.

In the three year period ending 1980, over 80 women have died of toxic shock. The Centers for Disease Control claim that tampons are associated with toxic shock as this mysterious disease seems to predominate in menstruating women who use tampons. It has been suggested that toxic shock may be due to the growth of bacteria, particularly *Staphylococcus aureus,* in the menstrual fluid absorbed by the tampon during the period of use.

OBJECTS OF THE INVENTION

It is the object of this invention to provide means for inhibiting bacterial growth in tampons while in use.

It is a further object of this invention to provide means for inhibiting bacterial growth without decreasing the absorptive capacity or period of use of the tampon.

DESCRIPTION OF THE INVENTION

These objects can be accomplished by the following invention which involves incorporating in the tampon one or more substances that will create a hostile, but physiologically safe, environment to inhibit the growth of bacteria within and on the tampon during its use.

This invention involves incorporating in said tampon one or more physiologically safe, organic acids that are water soluble in the monomeric state such as: citric acid, glycolic acid, malic acid, tartaric acid and lactic acid. The compounds should be in an amount sufficient to maintain the fluids in the tampon at a pH of about 4.5 or less during the period of use. Preferably the pH should be maintained within the range of about 4.5 to 2.5 to inhibit the growth of pathogenic bacteria such as *Staphylococcus aureus.*

It is considered best to incorporate the organic acid in the absorbent material prior to assembling the tampon. This can be done merely by mixing the acid with the absorbent material in an amount sufficient to give about 200 to 600 milligrams of acid in each tampon. Incorporation of the organic acids can also be made by spraying the absorbent material with an aqueous solution of the organic solid followed by drying the absorbent material prior to assembling the tampon; other methods of incorporating the organic acids will be evident to one skilled in the art without departing from the invention in its broader aspects.

This invention includes the use of the respective acids in the monomeric form as well as the oligomers and polymers of the respective acids either per se or in combination with the monomeric acid, and if a more rapid release of the polymeric acid is wanted, a suitable hydrolytic enzyme can be incorporated in the tampon to hydrolyze the polymeric acid to the monomeric form. The polymeric acids would be in the form of powder, granules or extruded fibers incorporated in the fibrous mass of the tampon. Such use of oligomeric and polymeric acids provides a slow release of organic acid and hence assures a regulated supply of acid during the use of the tampon. Where such oligomers or polymers are used, the amount needed would be about $\frac{1}{4}$ to $\frac{1}{2}$ of the amount needed of the monomeric acid.

With the pH of the fluids in the tampon maintained within the range of about 4.5 to 2.5, the bacterial growth responsible for toxic shock would be inhibited and the toxic shock thereby prevented. As the process is one of inhibiting pathogenic bacterial growth, normal bacteria in the vagina will not be destroyed. A pH of 4.5 is conducive to the growth of the beneficial bacteria that assist in preventing unwanted vaginal infections.

Examples of the polymeric forms of the organic acids suggested for use are polylactic and polyglycolic acids, and or copolymers of polylactic and polyglycolic acids. The recommended enzymes suggested for use would be from the class of hydrolases suited to function at an acid pH such as peptide peptido hydrolases, for example, trypsin and chymotrypsin.

Along with the use of physiologically safe organic acids, it is possible to add 5 to 30 milligrams of sodium benzoate or sodium propionate per tampon to further prevent bacterial growth in combination with the acid(s).

It is apparent that changes and modifications may be made without departing from the invention in its broader aspects. The aim of the appended claims, therefore, is to cover all such changes and modifications as fall within the true spirit and scope of the invention.

We claim:

1. A tampon having incorporated therein one or more organic acids selected from the group consisting of citric, glycolic, malic, tartaric and lactic acids, in combination with at least one of the group consisting of oligomer and polymer derivatives of said acids, said acids, and derivatives being present in an amount sufficient to maintain a pH of about 4.5 or less in the fluids absorbed during use of the tampon, whereby to inhibit the growth of pathogenic bacteria.

2. The tampon of claim 1 wherein there is also present 5 to 30 milligrams of sodium benzoate or sodium propionate in each tampon.

3. The tampon of claim 1 wherein the acids in the polymeric state are in the form of fibers.

4. The tampon of claim 1 wherein, when there are acids present in the oligomeric or polymeric state, there is also present a suitable hydrolytic enzyme that will hydrolyze such acids in to the monomeric form.

5. The tampon of claim 4 wherein there is also present 5 to 30 milligrams of sodium benzoate or sodium propionate in each tampon.

* * * * *